(12) United States Patent
Thuemen et al.

(10) Patent No.: US 12,004,713 B2
(45) Date of Patent: Jun. 11, 2024

(54) CONNECTION BODY OF AN ENDOSCOPE AND METHOD FOR ASSEMBLING AN ENDOSCOPE

(71) Applicant: OLYMPUS WINTER & IBE GMBH, Hamburg (DE)

(72) Inventors: Alrun Thuemen, Hamburg (DE); Uwe Schoeler, Hoisdorf (DE); Jens Schnitger, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 465 days.

(21) Appl. No.: 17/371,236

(22) Filed: Jul. 9, 2021

(65) Prior Publication Data

US 2021/0330176 A1    Oct. 28, 2021

Related U.S. Application Data

(63) Continuation of application No. PCT/EP2020/050066, filed on Jan. 3, 2020.

(30) Foreign Application Priority Data

Jan. 9, 2019   (DE) .......................... 102019100395.4

(51) Int. Cl.
   *A61B 1/00*      (2006.01)
   *H05K 1/18*      (2006.01)

(52) U.S. Cl.
   CPC ...... *A61B 1/00124* (2013.01); *A61B 1/00066* (2013.01); *A61B 1/0011* (2013.01);
   (Continued)

(58) Field of Classification Search
   CPC ............ A61B 1/00124; A61B 1/00066; A61B 1/0011; A61B 1/00128; H05K 1/189; H05K 2201/10053
   (Continued)

(56) References Cited

U.S. PATENT DOCUMENTS 10,939,803 B2    3/2021   Viebach et al.
2007/0211426 A1*  9/2007   Clayton ................ H01L 23/473
                                                    361/689

(Continued)

FOREIGN PATENT DOCUMENTS

DE   102010039731 A1   3/2012
DE   102012202133 A1   8/2013

(Continued)

OTHER PUBLICATIONS

International Search Report dated Mar. 12, 2020 issued in PCT/EP2020/050066.

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

A connection body for use with an endoscope that provides an electrical connection between at least one electrical component arranged in a proximal end region of the endoscope and an internal electrical connection provided in the proximal end region. The connection body including: a dimensionally stable three-dimensional circuit carrier: and a flexible elongate circuit board. Where, in a first region of the circuit carrier, the electrical component is mechanically directly connected to the circuit carrier and is contacted by conductor tracks provided in the circuit carrier; in a second region different from the first region, a first end of the circuit board is mechanically directly connected to the circuit carrier and contacts the conductor tracks for electrical connection to the electrical component and a second end of the circuit board opposite the first end in a longitudinal direction of the circuit board, contacts the internal electrical connection.

9 Claims, 5 Drawing Sheets

(52) U.S. Cl.
CPC ......... *A61B 1/00128* (2013.01); *H05K 1/189* (2013.01); *H05K 2201/10053* (2013.01)

(58) Field of Classification Search
USPC ........................................................ 600/132
See application file for complete search history.

(56) References Cited

U.S. PATENT DOCUMENTS

| | | |
|---|---|---|
| 2013/0158350 A1 | 6/2013 | Juergens |
| 2014/0066715 A1 | 3/2014 | Nagaoka |
| 2014/0371530 A1 | 12/2014 | Wieters et al. |
| 2017/0078583 A1 | 3/2017 | Haggerty et al. |
| 2017/0303419 A1* | 10/2017 | Collins .................. A61B 90/98 |

FOREIGN PATENT DOCUMENTS

| | | | |
|---|---|---|---|
| DE | 102013224683 A1 | 6/2015 | |
| DE | 102017101932 B3 | 6/2018 | |
| EP | 1958564 A2 * | 8/2008 | ......... A61B 1/00114 |
| EP | 1958564 A2 | 8/2008 | |
| EP | 2767213 A1 | 8/2014 | |

* cited by examiner

CONNECTION BODY OF AN ENDOSCOPE AND METHOD FOR ASSEMBLING AN ENDOSCOPE

CROSS-REFERENCE TO RELATED APPLICATION

The present application is a continuation of PCT/EP2020/050066 filed on Jan. 3, 2020, which is based upon and claims the benefit to DE 10 2019 100 395.4 filed on Jan. 9, 2019, the entire contents of each of which are incorporated herein by reference.

BACKGROUND

Field

The present disclosure relates to a connection body of an endoscope, which provides an electrical connection between at least one electrical component arranged in a proximal end region of the endoscope and an internal electrical connection provided in the proximal end region. The present disclosure additionally relates to a method for assembling an endoscope, in which such a connection body is deployed.

Prior Art

Medical endoscopes frequently have, in the region of their proximal end, that is to say in the region of or close to the handle which is held by the user when using the endoscope, switches or buttons in order to select or control various functions of the endoscope. Conventionally, such buttons are soldered onto a flexible circuit board which is fixed to a holding element provided inside the endoscope, for example by means of screws or the like. It has, however, emerged that the functionality of such operating elements can reduce over the course of time.

In addition to conventional circuit boards which can have both a dimensionally stable and flexible design, injection-molded circuit carriers which are also referred to as MID elements (MID=molded interconnected device) are known. Such injection-molded plastic components comprise metallic conductor tracks applied with special methods and serve as circuit carriers for electronic or mechatronic subassemblies.

An endoscope having a MID element is known from DE 10 2013 224 683 A1. At least one electronic instrument is seated on the MID element and is electrically supplied via conductor tracks of the MID element.

SUMMARY

It is an object to indicate an improved connection body of an endoscope and an improved method for assembling an endoscope.

Such object can be achieved by a connection body of an endoscope, which provides an electrical connection between at least one electrical component arranged in a proximal end region of the endoscope and an internal electrical connection provided in the proximal end region, wherein the internal electrical connection comprises a dimensionally stable three-dimensional circuit carrier and a flexible elongate circuit board, wherein in a first region of the circuit carrier, the at least one component is mechanically directly connected to the circuit carrier and is contacted by conductor tracks comprised by the circuit carrier, and in a second region of the circuit carrier, which differs from the first region, a first end of the flexible circuit board is mechanically directly connected to the circuit carrier and contacts the conductor tracks comprised by the circuit carrier for electrical connection to the at least one component, the second end, which is opposite the first end in a longitudinal direction, contacts the internal electrical connection or provides same.

The connection body can provide a double function. In this regard, the connection body can serve, on the one hand, as a mechanical holding device for the at least one electrical component. To this end, the connection body comprises the dimensionally stable three-dimensional circuit carrier. On the other hand, the connection body can serve as a flexible elongate circuit board which is connected to the dimensionally stable three-dimensional circuit carrier, as a flexible electrical connection element. The electrical connection provided on the second end of the flexible circuit carrier can be located in a region of the endoscope which is configured to be movable (for example rotatable) with respect to a further region, in which the dimensionally stable circuit carrier is present. This is, for example, typically the case between a distal part of the endoscope and the handle. In the relevant distal part, the endoscope has, for example, a rotating wheel or the like which can be rotated with respect to the handle of the endoscope about the longitudinal axis of the endoscope shaft. The elongate flexible circuit board can, for example, connect the dimensionally stable three-dimensional circuit carrier present in the rotatable part to an electrical connection provided in the region of the handle.

In addition, the dimensionally stable circuit carrier can combine both the function of a mechanical holding element for the electrical components and the function of a circuit board. The dimensionally stable circuit carrier can also have a double function.

At the same time, the dimensionally stable circuit carrier can remedy the problems which occur in the case of conventional constructions, which are significantly caused by tolerances between a mechanical holding element and the traditionally used circuit board, on which the components are provided. It has of course been discovered that the change in the reliability of the functionality of the operating elements which can be ascertained in some cases over the course of time can be substantially caused by the manufacturing tolerances which cannot be avoided between the circuit board and the mechanical holding element. During the course of the lifetime of the endoscope, for example as a consequence of preparation processes and the thermal stresses connected therewith, changes can occur in the assembly position of the circuit board and, therefore, of the electrical components. It can then happen that a component no longer functions reliably in its changed position since, for example, an outer cap or cover no longer interacts with the component in an ideal manner. Since the dimensionally stable circuit carrier is both a mechanical holding element and provides the electrical connections, such effects are practically excluded.

The circuit carrier can be, for example, produced from a plastic which is suitable for laser direct structuring. A suitable material is, for example, PEEK.

The conductor tracks of the dimensionally stable three-dimensional circuit carrier can be, for example, produced in a laser direct structuring method. A layer system made of copper, nickel and gold is, for example, deployed as a material for the conductor tracks. That is to say, it is therefore, for example, a layer system having three layers made of copper, nickel and gold which can be arranged in any order. The conductor tracks are, for example, applied using a currentless coating method. The circuit carrier is additionally, for example, an injection-molded part. The circuit carrier is thus, for example, a dimensionally stable three-dimensional injection-molded circuit carrier. It is, however, likewise provided that the circuit carrier can be a component produced by means of 3D printing. The at least one component is electrically connected by means of a solder connection to at least one of the conductor tracks of the circuit carrier.

According to an embodiment, the electrical component can be an electrical switch. For example, the electrical switch is a button or pressure switch. Other electronic devices are likewise provided. These can be, for example, resistors, capacitors or a wide range of integrated circuits (ICs). Likewise, a LED can, for example, be provided for a display or an illuminated button.

Since an electrical switch interacts in many cases with an outer operating element such as, for example, a cap or the like, the reliable positioning of an electrical switch can be important in order to guarantee and obtain its functionality.

According to an embodiment, the at least one electrical component can be arranged on an outside of the circuit carrier and the circuit carrier on an opposite inner side can be configured in a complementary manner to an internal proximal component of the endoscope at least in sections.

The circuit carrier can be fixed axially, i.e., in the longitudinal axial direction of the endoscope (the latter will frequently correspond to a direction of longitudinal extent of a shaft of the endoscope) and in a rotational direction. The rotational direction frequently corresponds to a circumferential direction of the shaft. This fixing is effected, for example, by suitable latching connections. A fixing by a positive connection is provided. Such a configuration of the circuit carrier makes possible precise positioning inside the endoscope. The functional reliability of the electrical components is improved. This is especially due to the fact that a slippage of the electrical components provided on the circuit carrier with respect to outer operating elements (for example caps and the like) in the axial direction and in the circumferential direction is prevented. Consequently, an optimal mechanical interaction between the outer operating elements and the electrical components is ensured.

According to a further embodiment, the positive connection can be formed by overmolding. In this case, the connection body can be molded around a supporting component of the endoscope in the proximal end region of the endoscope. This is especially advantageous if mechanical forces act on the joint.

According to a further embodiment, the circuit carrier can be provided with fixing means which make it possible to assemble the connection body on the internal proximal component of the endoscope without tools.

A latching or click connection can be, for example, provided as a connection means. Said connections make it possible to put the endoscope together quickly and efficiently and can, in addition, be produced efficiently and economically. For example, the connection means can be, for example, latching arms, latching noses or the like configured in one piece with the dimensionally stable three-dimensional circuit carrier.

According to a further embodiment, the flexible circuit board can comprise at least one through-connection (also referred to as a via) running along an outer edge of the circuit board, wherein the circuit board is electrically connected to a conductor track of the carrier body by means of a solder connection connecting said through-connection.

The linking, that is to say mechanical connection, and contacting of the circuit board via such edge vias facilitates the soldering process in a very substantial manner.

It is additionally provided that the soldering position of the electrical components and/or of the flexible conductor track can be predefined by correspondingly mounted reference structures, for example stops, markings or the like, with respect to the dimensionally stable three-dimensional circuit carrier. This likewise facilitates the process of putting the endoscope together.

According to a further embodiment, the at least one electrical component can be arranged on an outside of the circuit carrier and the flexible circuit board on an opposite inner side of the circuit carrier can be electrically and mechanically connected to the circuit carrier.

The circuit carrier can be arranged, for example in the region of a handle of the endoscope, on a casing tube provided in this region in the interior of the endoscope.

According to a further embodiment, the flexible circuit board can be guided between a fiber tube and a casing tube of the endoscope to the electrical connection.

Such object can be further achieved by a method for assembling an endoscope, in which a connection body according to one or more of the previously indicated embodiments is assembled on a proximal component of the endoscope without tools and an electrical contact is produced between the electrical component and the internal electrical connection provided in the proximal end region of the endoscope.

The connection body can be configured such that the connection body is provided with fixing means which make it possible to assemble the connection body on the internal component of the endoscope without tools.

The method makes it possible to put the endoscope together quickly and efficiently.

In other respects, the same or similar advantages which have already been mentioned with respect to the connection body itself apply to the method.

BRIEF DESCRIPTION OF THE DRAWINGS

Further features will become evident from the description of embodiments, together with the claims and the appended drawings. Embodiments can fulfil individual features or a combination of multiple features.

The embodiments are described below without limiting the general concept of the invention by means of exemplary embodiments with reference to the drawings, wherein reference is expressly made to the drawings regarding all of the details which are not explained in greater detail in the text, wherein.

In the drawings, the same or similar elements and/or parts are, in each case, provided with the same reference numerals such that they are not introduced again in each case.

DETAILED DESCRIPTION

Figure 1:
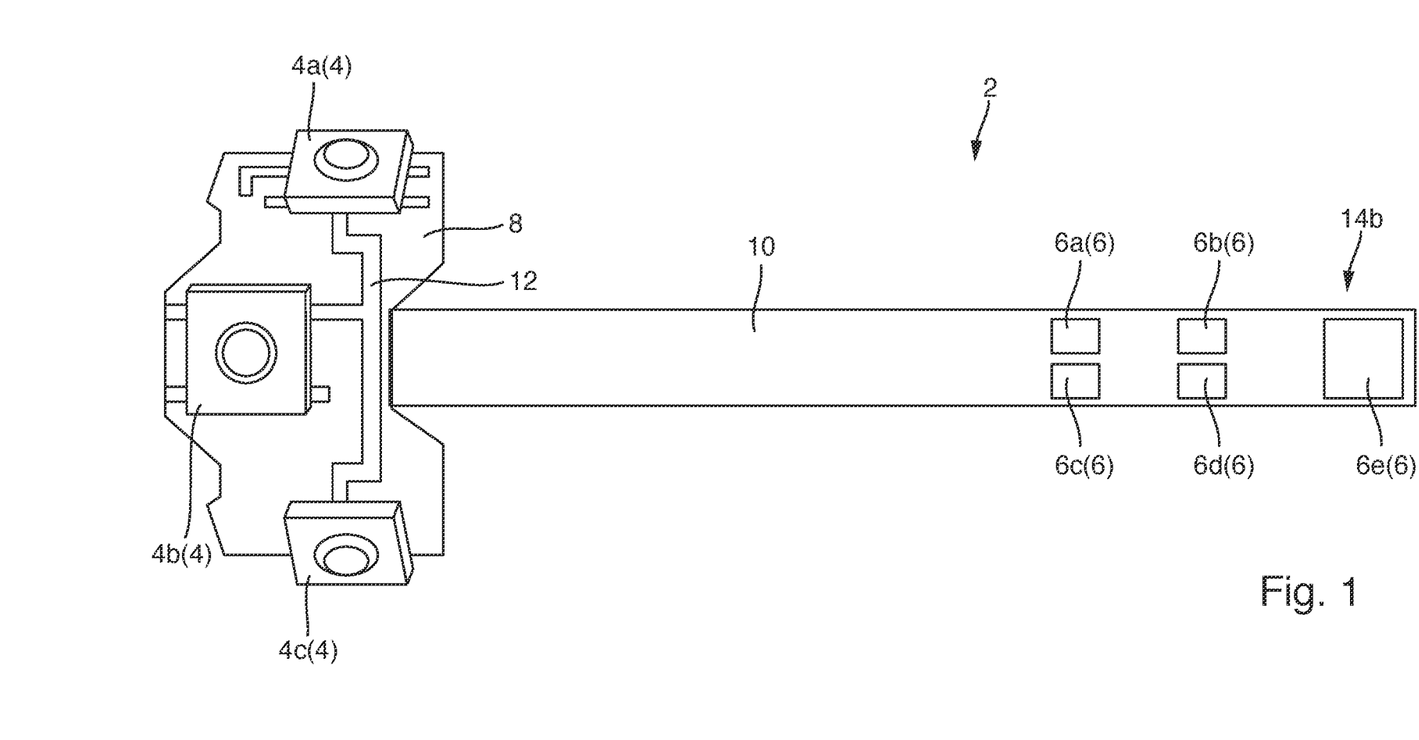
FIG. 1 illustrates a schematic and simplified top view of the connection body from the upper side.

FIG. 1 shows a schematic and simplified top view of a connection body 2 of an endoscope. The connection body 2 is arranged in a proximal end region of the endoscope. It provides an electrical connection between an electrical component 4 which is provided in a proximal end region of the endoscope, and an internal electrical connection 6. By way of example, the electrical component 4 can be an electrical switch. A first, second and third pressure switch 4a, 4b, 4c are additionally depicted, for example, as electrical switches in FIG. 1. The electrical connection 6 is formed by schematically indicated connection contacts 6a . . . 6e. The connection body 2 comprises a dimensionally stable three-dimensional circuit carrier 8 and a flexible elongate circuit board 10.

The circuit carrier 8 is, for example, an injection-molded part. It can, however, likewise be a component produced by means of 3D printing. The circuit carrier 8 is, for example, produced from a plastic which is suitable for laser direct structuring. A possible plastic material is PEEK. Following the laser structuring, conductor tracks 12 are applied to the circuit carrier 8, for example with a currentless coating method. A layer system having three layers made of copper, nickel and gold is, for example, provided as the material for the conductor tracks 12, wherein the individual layers can be arranged in any order. The electrical components 4 in the form of the pressure switches 4a, 4b and 4c are mechanically and electrically directly connected to the circuit carrier 8 in different regions thereof. The circuit carrier 8 thus serves as a mechanical holding element for the components 4, on the one hand, and as an electrical connection element for these on the other hand. To this end, the contacts of the components 4 are contacted by the conductor tracks 12, for example by means of solder connections.

Figure 2:
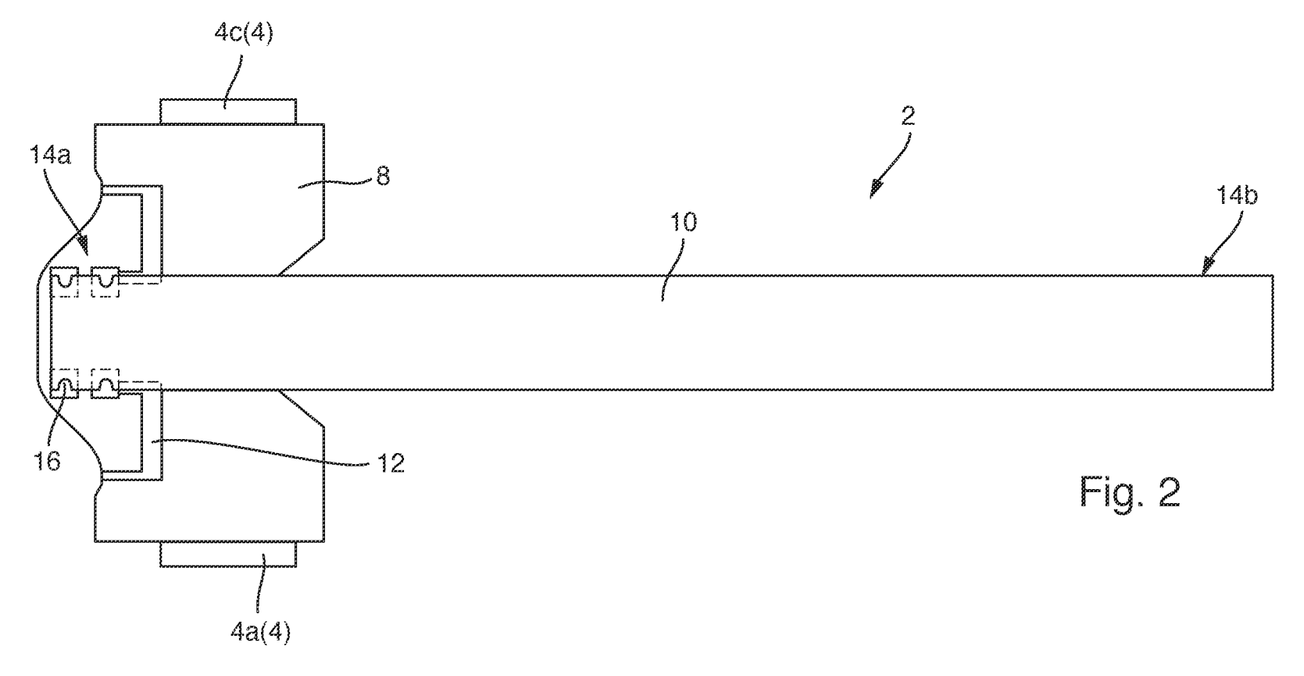
FIG. 2 illustrates a schematic and simplified top view of the connection body from the lower side.

FIG. 2 likewise shows a schematically simplified top view of the connection body 2 from its lower side. A first end 14a of the flexible circuit board 10 is mechanically and electrically directly connected to the circuit carrier 8 on its lower side. To this end, solder connections are, for example, provided between the first end 14a of the flexible circuit board 10 and contacts provided on the lower side of the circuit carrier 8. Such contacts are to be deemed to be part of the conductor tracks 12. While the electrical components 4 (FIG. 1) are arranged on an outside of the connection body 2, the flexible circuit board 10 contacts the circuit carrier 8 on its inner side (FIG. 2). Conductor tracks 12 provided in the flexible circuit board 10, which are not depicted, connect the contacts provided on the first end 14a to the connection contacts 6a . . . 6e of the electrical connection 6 (FIG. 1), which are located in the region of a second end 14b of the flexible circuit board 10.

The flexible circuit board 10 has, for example, through-connections 16 (edge vias) running on its outer edges in the region of the first end 14a on its outside (side edge), on which through-connections the flexible circuit board 10 contacts the conductor tracks 12 of the circuit carrier 8. Said through-connections 16 are indicated by indentations in FIG. 2.

The lower side or inner side of the circuit carrier 8, which is visible in FIG. 2, is configured in a complementary manner to an internal proximal component of the endoscope at least in sections.

Figure 3:
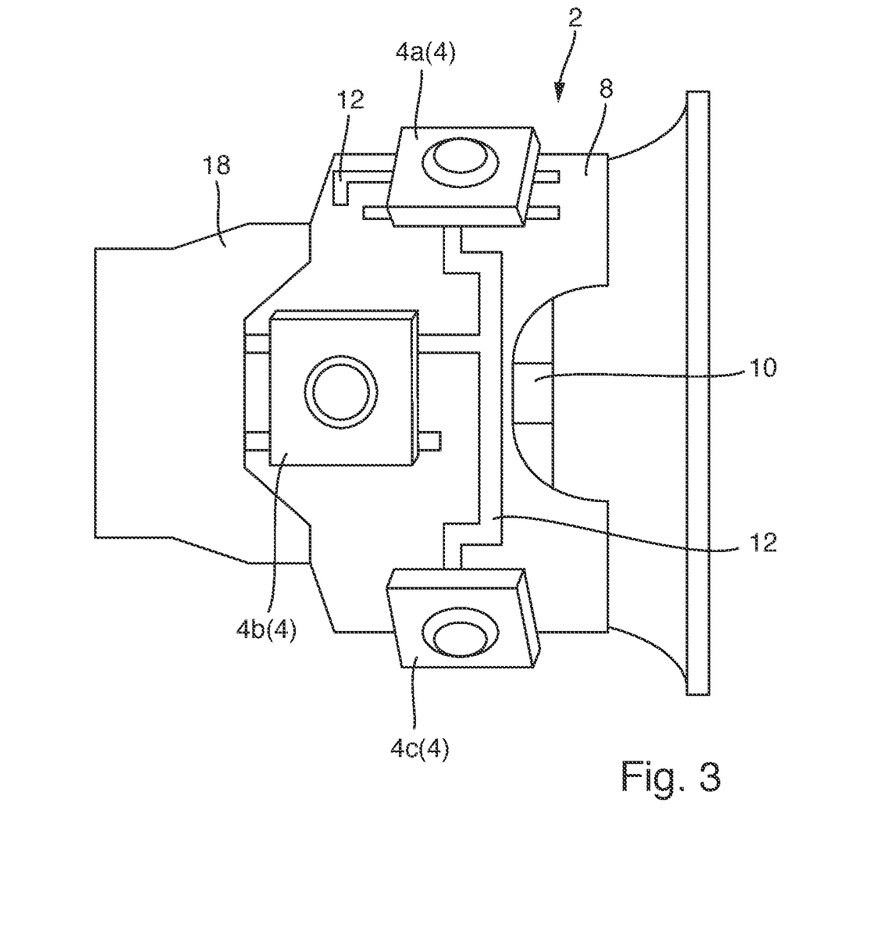
FIG. 3 illustrates a schematic and simplified perspective representation of a connection body in the assembled condition in an endoscope, wherein the dimensionally stable three-dimensional circuit carrier is assembled in the proximal end region of the endoscope.

FIG. 3 shows a schematic and simplified perspective representation of the connection body 2 in the assembled condition. The circuit carrier 8 is assembled in the proximal end region of the endoscope and positioned, by way of example, on a casing tube 18 of the endoscope. The flexible circuit board 10, which is merely visible in sections, extends in the proximal direction (towards the right in FIG. 3) and provides an electrical connection 6 which is located further proximally in the interior of the endoscope, on its second end 14b. The electrical connection 6 can, for example, contact a plug or the like provided at the end of the handle. The circuit carrier 8 is provided with fixing or holding means which make it possible to assemble the connection body 2 on the internal proximal component of the endoscope, in this case on the casing tube 18, without tools. For example, latching hooks are provided for this purpose.

Figure 4:
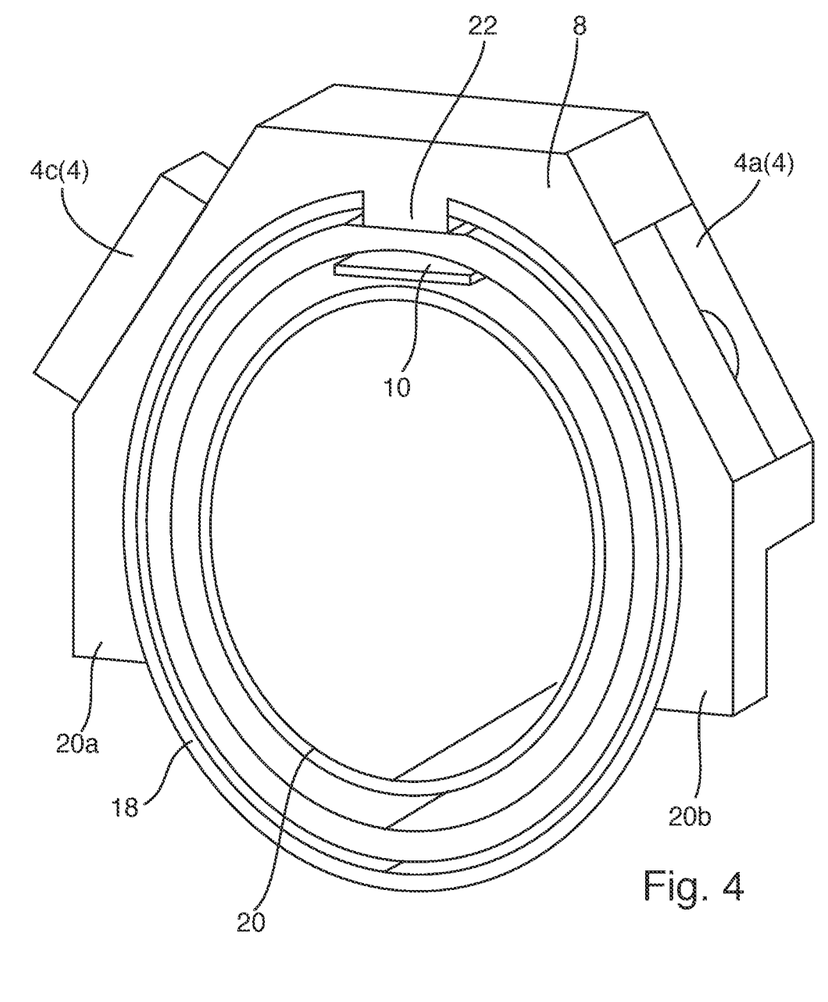
FIG. 4 illustrates a further schematic and simplified perspective sectional view in a plane perpendicular to a longitudinal axial direction of the endoscope shaft, wherein the dimensionally stable three-dimensional circuit carrier of the connection body and the elongate flexible circuit board are likewise depicted in a sectional manner.

FIG. 4 shows a schematic and simplified perspective sectional view in a plane which lies at least approximately perpendicular to a longitudinal axial direction of the endoscope shaft. The circuit carrier 8 including the electrical components 4 as well as the flexible circuit board 10 and the casing tube 18 and a fiber tube 20 of the endoscope, which is located further inwards, are depicted in a sectional manner. The flexible circuit board 10 extends between the fiber tube 20 and the casing tube 18 of the endoscope in the longitudinal axial direction thereof. The circuit carrier 8 is configured in a complementary manner to an outside of the casing tube 18 on its inner side.

The circuit carrier 8 comprises two legs 20a, 20b which are located opposite one another, which bend slightly out of shape (from one another) when the circuit carrier 8 is placed on the casing tube 18, so that the circuit carrier 8 can be positioned on the casing tube 18 in the manner of a snap connection. To ensure that the circuit carrier 8 is fixed both in the axial direction and in the circumferential direction (rotationally) of the endoscope and its position is consequently defined, the latter has a latching nose 22 which engages positively in an opening of the casing tube 18 provided for this purpose. The connection body 2 can thus be assembled on the casing tube 18 of the endoscope without tools.

Figure 5:
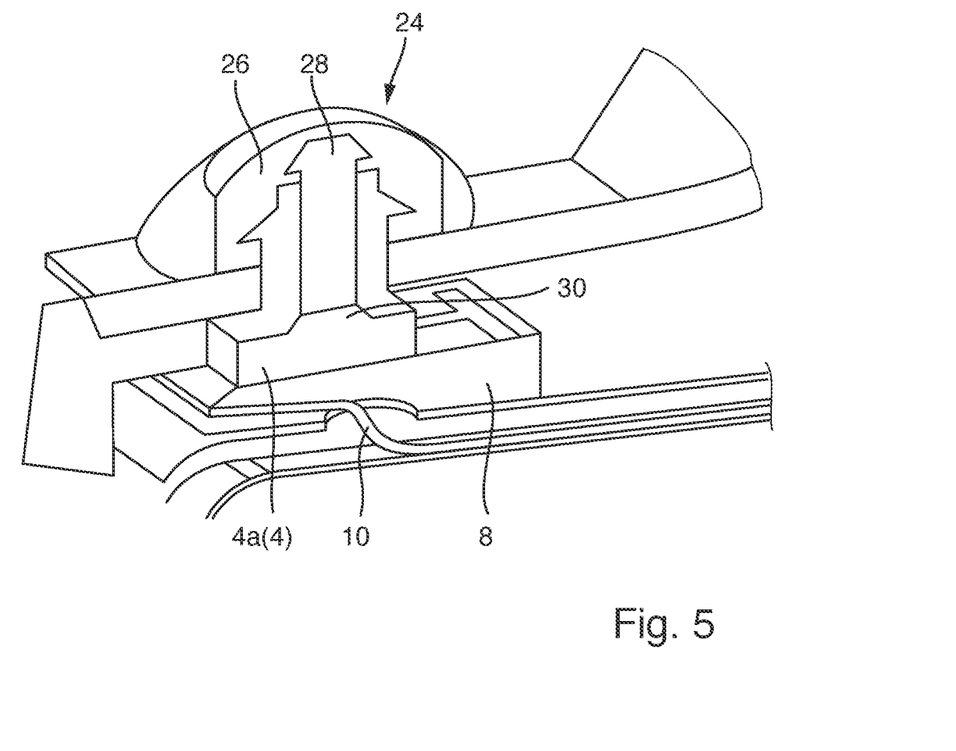
FIG. 5 illustrates a schematic and simplified perspective sectional view of an assembled connection body in the region of an electrical component provided on the dimensionally stable three-dimensional circuit carrier.

FIG. 5 shows a schematic and simplified perspective sectional view of the assembled circuit carrier 8, on the outside of which the first pressure switch 4a is visible as an exemplary electrical component 4. In order to operate the pressure switch 4a, the endoscope has on its outside an operating button 24. This is a pushbutton which comprises a flexible dome 26, for example made of rubber, into which a punch 28 is inserted. The punch 28 interacts with a contact button 30 of the first pressure switch 4a. The pressure switch 4a is mechanically and electrically connected to the circuit carrier 8 which is in turn securely fixed on the casing tube 18 by means of the positive connection just described. The alignment between the punch 28 and the contact button 30 can be securely and reliably produced thanks to said construction. This is the case even after many preparation and usage cycles.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMERALS

2 Connection body
4 Component
4a, 4b, 4c Pressure switch
6 Electrical connection
6a . . . 6e Connection contacts
8 Circuit carrier
10 Flexible circuit board
12 Conductor tracks
14a First end
14b Second end
16 Through-connection
18 Casing tube
20 Fiber tube
20a, 20b Leg
22 Latching nose
24 Operating button
26 Dome
28 Punch
30 Contact button

What is claimed is:

1. A connection body for use with an endoscope, the connection body providing an electrical connection between at least one electrical component arranged in a proximal end region of the endoscope and an internal electrical connection provided in the proximal end region, the connection body comprising:
 a dimensionally stable three-dimensional circuit carrier comprising conductor tracks: and
 a flexible elongate circuit board;
 wherein in a first region of the circuit carrier, the at least one electrical component is mechanically directly connected to the circuit carrier and is contacted by the conductor tracks provided in the circuit carrier;
 in a second region of the circuit carrier, which differs from the first region, a first end of the circuit board is mechanically directly connected to the circuit carrier and contacts the conductor tracks for electrical connection to the at least one electrical component; and
 a second end of the circuit board, which is opposite the first end in a longitudinal direction of the circuit board, at least indirectly contacts the internal electrical connection.

2. The connection body according to claim 1, wherein the electrical component is an electrical switch.

3. The connection body according to claim 1, wherein the at least one electrical component is arranged on an outside of the circuit carrier and the circuit carrier on an opposite inner side is configured in a complementary manner to an internal proximal component of the endoscope at least in sections.

4. The connection body according to claim 3, wherein the circuit carrier is provided with a latch configured to assemble the connection body on the internal proximal component of the endoscope without tools.

5. The connection body according to claim 1, wherein the circuit board comprises at least one through-connection running along an outer edge of the circuit board, wherein the circuit board is electrically connected to a conductor track of the carrier body by means of a solder connection connecting the through-connection.

6. The connection body according to claim 1, wherein the at least one electrical component is arranged on an outside of the circuit carrier and the circuit board arranged on an opposite inner side of the circuit carrier is electrically and mechanically connected to the circuit carrier.

7. The connection body according to claim 1, wherein the circuit board is guided between a fiber tube and a casing tube of the endoscope to the electrical connection.

8. The connection body according to claim 1, wherein the circuit carrier having an annular shape with an internal hole.

9. A method for assembling an endo scope, in which a connection body according to claim 4 is assembled on a proximal component of the endoscope without tools and an electrical contact is produced between the electrical component and the internal electrical connection provided in the proximal end region of the endoscope.

* * * * *